(12) United States Patent
Henderson

(10) Patent No.: US 7,682,386 B2
(45) Date of Patent: *Mar. 23, 2010

(54) COUNTER ROTATIONAL LAYERING OF EPTFE TO IMPROVE MECHANICAL PROPERTIES OF A PROSTHESIS

(75) Inventor: Jamie S. Henderson, Oakland, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 561 days.

This patent is subject to a terminal disclaimer.

(21) Appl. No.: 11/410,116

(22) Filed: Apr. 24, 2006

(65) Prior Publication Data

US 2006/0195174 A1 Aug. 31, 2006

Related U.S. Application Data

(60) Continuation of application No. 10/775,442, filed on Feb. 10, 2004, now Pat. No. 7,056,412, which is a division of application No. 09/990,422, filed on Nov. 21, 2001, now Pat. No. 6,719,784.

(51) Int. Cl.
*A61F 2/06* (2006.01)
(52) U.S. Cl. .................... 623/1.39; 623/1.44; 623/1.42
(58) Field of Classification Search ................ 623/1.39, 623/1.44, 1.49, 1.54, 23.64, 23.71, 1.13, 623/901; 156/165
See application file for complete search history.

(56) References Cited

U.S. PATENT DOCUMENTS

| 2,667,852 | A | | 2/1954 | Brown, Jr. |
| 2,945,265 | A | | 7/1960 | Sell, Jr. et al. |
| 3,008,187 | A | | 11/1961 | Slade |
| 3,260,774 | A | | 7/1966 | Harlow |
| 3,307,017 | A | | 2/1967 | Horstmann |
| 3,730,229 | A | | 5/1973 | D'Onfrio |
| 3,893,878 | A | | 7/1975 | Kaempen |
| 4,104,394 | A | | 8/1978 | Okita |
| 4,225,547 | A | | 9/1980 | Okita |
| 4,550,447 | A | * | 11/1985 | Seiler et al. ................. 623/1.32 |
| 4,743,480 | A | | 5/1988 | Campbell et al. |
| 4,876,051 | A | | 10/1989 | Campbell et al. |
| 5,156,785 | A | | 10/1992 | Zdrahala |
| 5,282,847 | A | * | 2/1994 | Trescony et al. ........... 623/1.29 |
| 5,450,860 | A | * | 9/1995 | O'Connor .................... 128/898 |
| 5,505,887 | A | | 4/1996 | Zdrahala et al. |
| 5,609,624 | A | * | 3/1997 | Kalis .......................... 623/1.32 |
| 5,788,626 | A | | 8/1998 | Thompson |
| 5,800,512 | A | | 9/1998 | Lentz et al. |
| 5,800,522 | A | * | 9/1998 | Campbell et al. ........... 128/898 |
| 5,824,046 | A | | 10/1998 | Smith et al. |

(Continued)

FOREIGN PATENT DOCUMENTS

EP 0775472 A 5/1997

(Continued)

Primary Examiner—Paul Prebilic
(74) Attorney, Agent, or Firm—Vidas, Arrett & Steinkraus P.A.

(57) ABSTRACT

A prosthesis, and method for forming same, are provided which includes expanded polytetrafluoroethylene (ePTFE) tubes having angularly offset node and fibril configurations. Also, the node and fibril configurations are angularly offset from the longitudinal axes of the respective tubes, providing resistance against failure in the longitudinal direction.

13 Claims, 4 Drawing Sheets

U.S. PATENT DOCUMENTS

| | | |
|---|---|---|
| 5,874,032 A | 2/1999 | Zdrahala et al. |
| 5,891,108 A | 4/1999 | Leone et al. |
| 5,928,279 A | 7/1999 | Shannon et al. |
| 6,027,779 A | 2/2000 | Campbell et al. |
| 6,042,605 A * | 3/2000 | Martin et al. ............... 623/1.13 |
| 6,403,887 B1 * | 6/2002 | Kebabjian et al. ....... 174/110 R |
| 6,451,047 B2 * | 9/2002 | McCrea et al. .............. 623/1.13 |
| 6,719,784 B2 * | 4/2004 | Henderson .................. 623/1.44 |
| 7,056,412 B2 * | 6/2006 | Henderson .................. 156/294 |
| 2001/0039446 A1 * | 11/2001 | Edwin et al. ................ 623/1.13 |
| 2002/0049489 A1 | 4/2002 | Herweck et al. |

FOREIGN PATENT DOCUMENTS

| | | |
|---|---|---|
| GB | 2204945 | 11/1988 |
| WO | WO 97/02791 A | 1/1997 |
| WO | WO 00/43052 A | 7/2000 |
| WO | WO-00/43052 A1 * | 7/2000 |

* cited by examiner

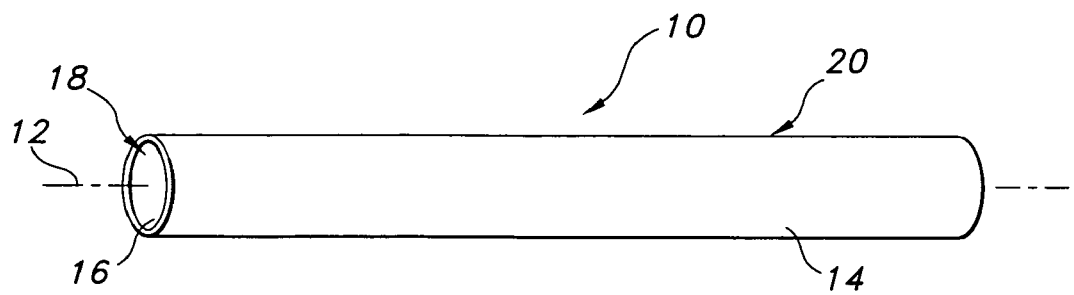
FIG. 1
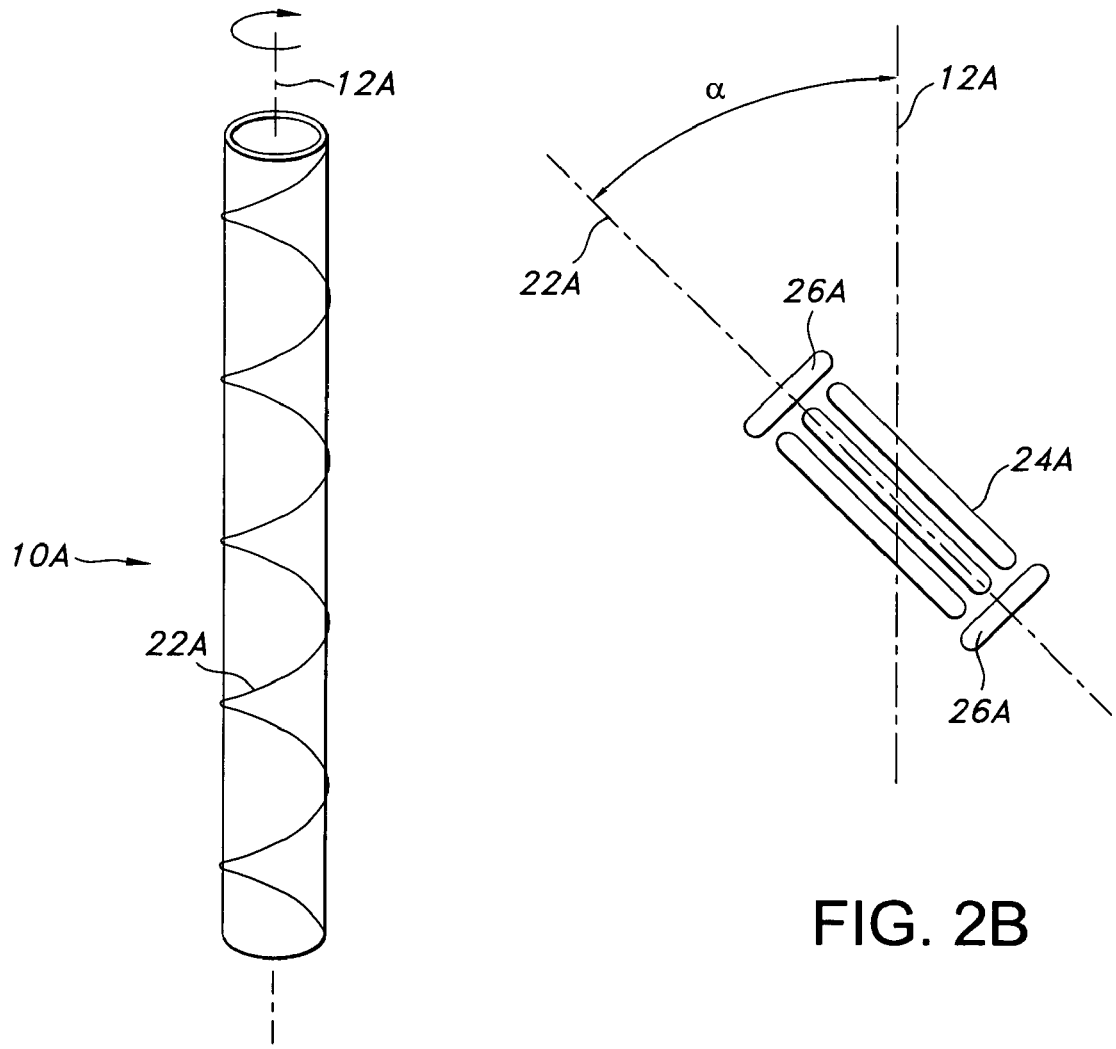
FIG. 2A
FIG. 2B

COUNTER ROTATIONAL LAYERING OF EPTFE TO IMPROVE MECHANICAL PROPERTIES OF A PROSTHESIS

CROSS-REFERENCE TO RELATED APPLICATIONS

This application is a continuation of U.S. application Ser. No. 10/775,442, filed Feb. 10, 2004, now U.S. Pat. No. 7,056,412, which is a division of U.S. application Ser. No. 09/990,422, filed Nov. 21, 2001, now U.S. Pat. No. 6,719,784, which are incorporated herein by reference.

FIELD OF THE INVENTION

This invention relates to methods of preparing tubular prostheses, and, more particularly, to techniques for forming multi-layered prostheses.

BACKGROUND OF THE INVENTION

Formation of prostheses from polytetrafluoroethylene (PTFE), particularly expanded polytetrafluoroethylene (ePTFE) is well known in the prior art. ePTFE includes a node and fibril structure, having longitudinally extending fibrils interconnected by transverse nodes. The nodes are not particularly strong in shear, and, thus, ePTFE structures are susceptible to failure in a direction parallel to the fibril orientation. ePTFE structures (tubes, sheets) are typically paste extruded, and, the fibrils are oriented in the extrusion direction.

Vascular grafts formed of ePTFE are well known in the art. Where sutures have been used to fix such grafts, suture hole elongation and propagation of tear lines from suture holes have been noted.

To overcome the deficiencies of the prior art, techniques have been developed which re-orient the node and fibril structure of an ePTFE element to be transverse to the extrusion direction. By orienting the fibrils at an angle relative to the extrusion direction, the tear strength of a respective product may be greatly improved. In one technique set forth in U.S. Pat. Nos. 5,505,887 and 5,874,032, both to Zdrahala et al., an extrusion machine is described having a counter-rotating die and mandrel arrangement. Accordingly, upon being extruded, a single-layer unitary PTFE tube is formed having an outer surface twisted in one helical direction, and an inner surface twisted in an opposite helical direction. Although tubes formed in accordance with the method of U.S. Pat. Nos. 5,505,887 and 5,874,032 are expandable to form an ePTFE structure, the fibrils of the structure are oriented generally parallel to the expansion direction after expanding as shown in the micrograph of FIG. 5 in U.S. Pat. No. 5,874,032. Also, the tube tends to thin out unevenly under expansion, and, suffers from "necking".

SUMMARY OF THE INVENTION

To overcome the deficiencies of the prior art, a method is provided wherein ePTFE tubes are counter-rotated, coaxially disposed, and fixed one to another to form a composite multi-layer prosthesis. By rotating the tubes, the tubes each becomes helically twisted with its node and fibril configuration being angularly offset throughout from the longitudinal axis of the tube (and, thus, angularly offset from the extrusion direction of the tube). With counter-rotation, the nodes and fibrils of the two tubes are also angularly offset from each other, resulting in a relatively strong composite structure. The composite multi-layer structure is akin to plywood, where alternating layers have differently oriented grain directions.

These and other features will be better understood through a study of the following detailed description and accompanying drawings.

BRIEF DESCRIPTION OF DRAWINGS

FIG. 1 is an elevational view of an ePTFE tube;

FIG. 2A is an elevational view of a helically wound tube twisted in a first rotational direction;

FIG. 2B is a schematic of the node and fibril orientation of the first tube in a helically wound state;

DETAILED DESCRIPTION OF THE INVENTION

Figures 3A, 3B:
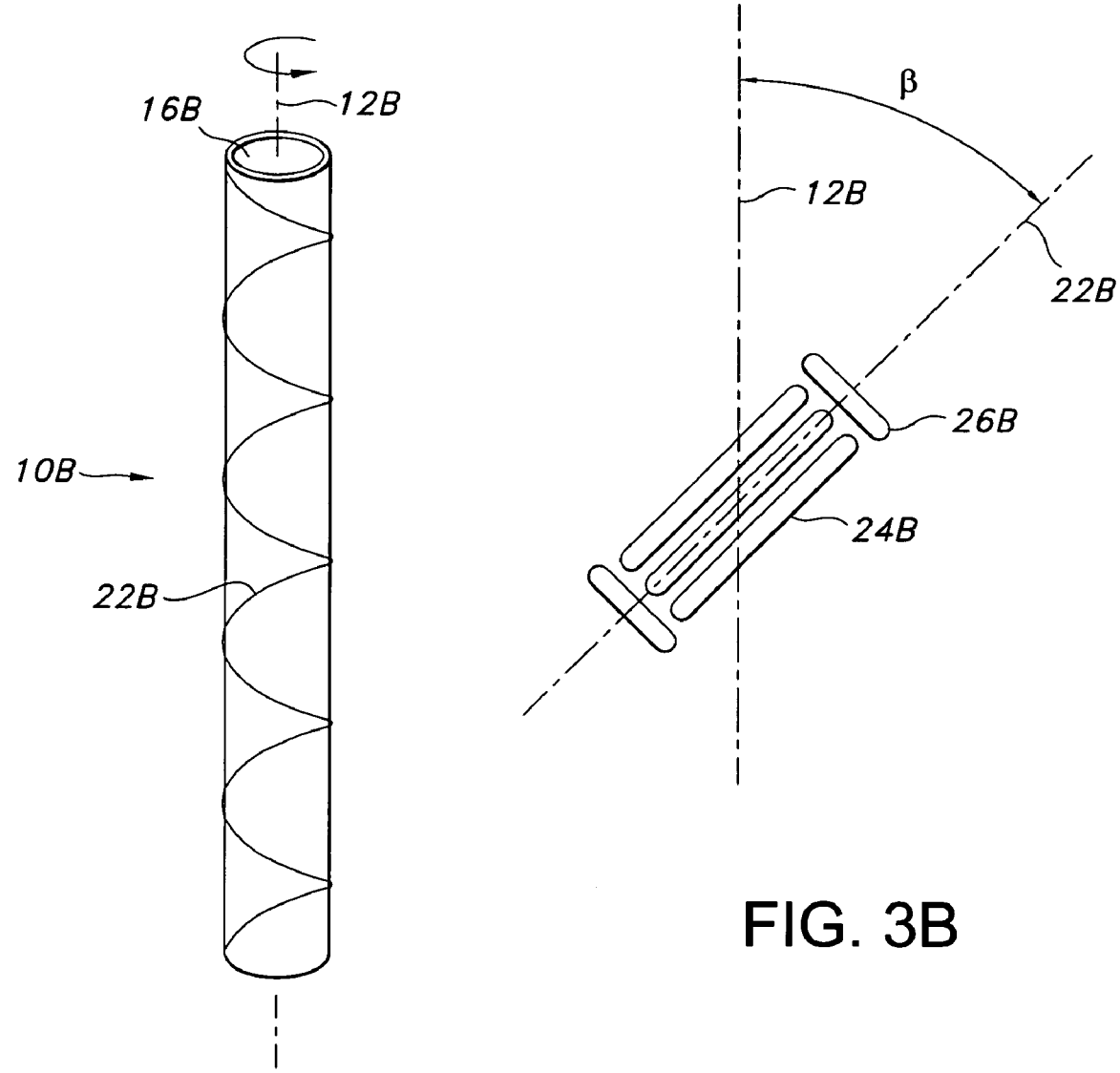
FIG. 3A is an elevational view of a helically wound tube twisted in a second rotational direction.
FIG. 3B is a schematic of the node and fibril orientation of the second tube in a helically wound state.

The invention herein provides a multi-layer prosthesis which may be used as a graft to replace a portion of a bodily passageway (e.g., vascular graft), or within a bodily passageway to maintain patency thereof, such as an endovascular stent-graft. In addition, the prosthesis can be used in other bodily applications, such as the esophagus, trachea, colon, biliary tract, urinary tract, prostate, and the brain.

The prosthesis is composed of multiple layers, including coaxially disposed ePTFE tubes. To illustrate the invention, reference will be made to the use of two ePTFE tubes, although any number may be utilized consistent with the principles disclosed herein. With reference to FIG. 1, an ePTFE tube 10 is shown which extends along a longitudinal axis 12. The ePTFE tube 10 is preferably formed by extrusion, thus having its fibrils generally parallel to the extrusion direction of the tube, which coincides with the longitudinal axis 12. The ePTFE tube 10 includes a wall 14 (which is seamless if extruded), that extends about a lumen 16. The wall 14 includes an inner luminal surface 18 facing the lumen 16, and an outer, abluminal surface 20. The ePTFE tube may be formed of any length and of various dimensions, although it is preferred that the dimensions be generally constant throughout the length thereof. In describing first and second tubes of the invention, like reference numerals will be used to describe like elements, but with the extensions "A" and "B" for differentiation. Elements associated with a first tube will have the extension "A", while elements associated with a second tube will have the extension "B".

Referring to FIG. 2A, a first ePTFE tube 10A is shown disposed along a longitudinal axis 12A. The first tube 10A is twisted about its longitudinal axis 12A in a first rotational direction, such as clockwise, as shown in FIG. 2A. The tube 10A may be twisted over any given range of degrees, although it is preferred that the tube be twisted at least 10 degrees. Accordingly, as represented by the hypothetical reference axis 22A, the first tube 10A is helically wound in the first rotational direction. As a result and as shown in FIG. 2B, fibrils 24A are generally parallel to the reference axis 22A, with the fibrils 24A being angularly offset an angle α from the longitudinal axis 12A, and, thus, being also angularly offset the angle α from the original extrusion direction of the first tube 10A. Nodes 26A are generally perpendicular to the fibrils 24A. With the fibrils 24A, and the nodes 26A, being obliquely disposed relative to the longitudinal axis 12A, failure along the longitudinal axis 12A may be reduced.

Referring to FIGS. 3A and 3B, a second ePTFE tube 10B is shown being twisted in a second rotational direction different than the first rotational direction of the first tube 10A. As shown in FIG. 3A, the second ePTFE tube is twisted in a counterclockwise direction. The particular rotational direction of twisting may be switched for the first and second tubes 10A and 10B. As with the first tube 10A, the amount of twisting of the second tube 10B may be varied, although it is preferred that at least a 10 degree displacement be provided. The helically wound distortion of the second tube 10B is represented by the hypothetical reference axis 22B. As shown in FIG. 3B, fibrils 24B are generally parallel to the reference axis 22B and are angularly offset an angle β from the longitudinal axis 12B (and, thus, the extrusion direction). Nodes 26B are generally perpendicular to the fibrils 26A. The oblique disposition of the fibrils 24B and the nodes 26B resists failure along the longitudinal axis 12B.

Figures 4A, 4B:
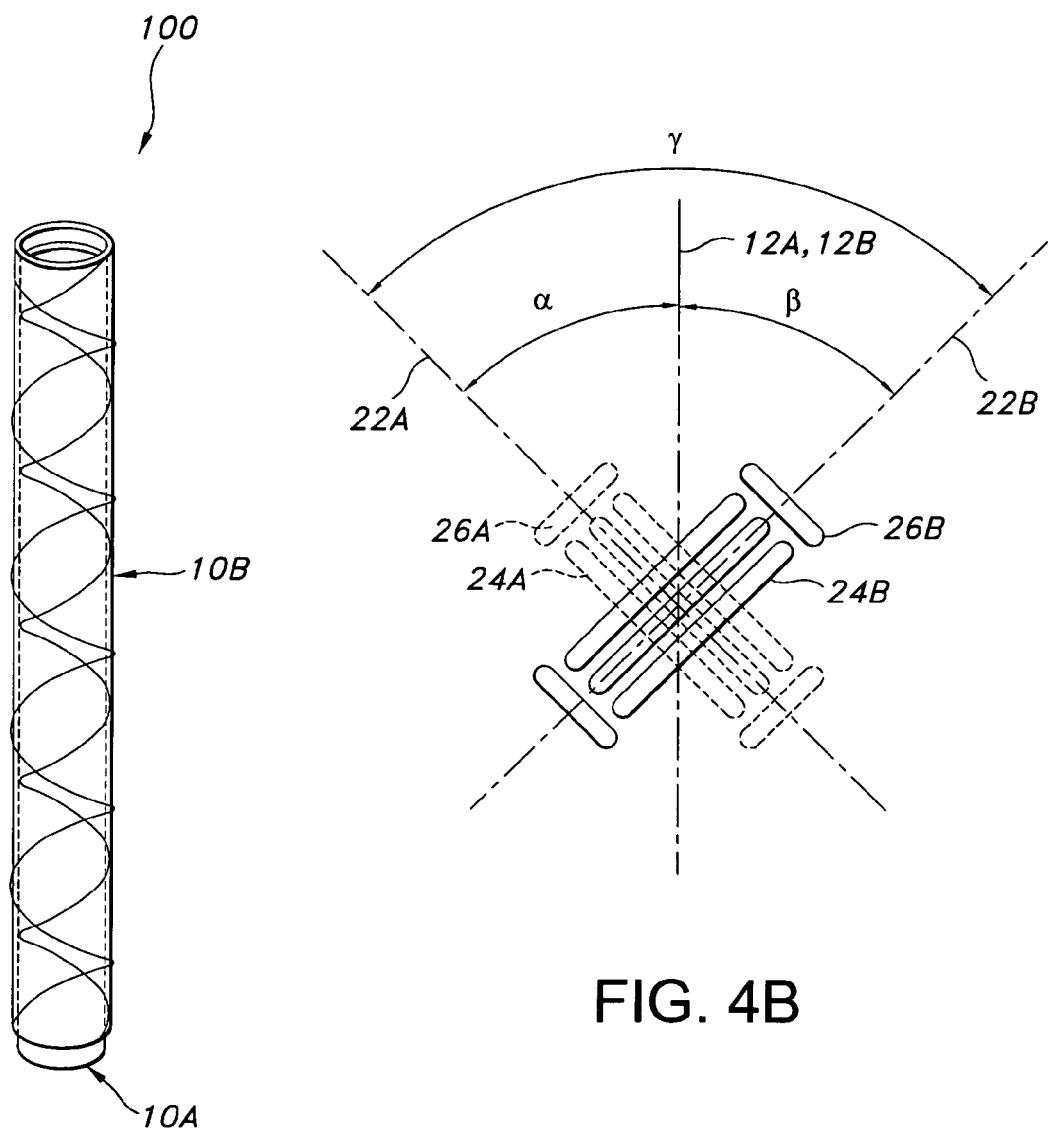
FIG. 4A is an elevational view of a prosthesis formed in accordance with the subject invention.
FIG. 4B is a schematic of the node and fibril orientations of the composite prosthesis; and, FIG. 5 is an exploded view of a prosthesis having a radially-expandable support member.

FIG. 4A shows a prosthesis 100 including the first tube 10A, in its twisted helical state being coaxially disposed within, and fixed to, the second tube 10B, in its twisted helical state. It is preferred that the tubes 10A and 10B be generally coextensive, although the ends of the tubes need not be coterminous. Because of the different rotational orientations of the node and fibril structures of the tubes 10A and 10B, the node and fibril structures are angularly offset from each other. In particular, as shown schematically in FIG. 4B, because of the coaxial arrangement of the tubes 10A, 10B, the longitudinal axes 12A and 12B are generally colinear. Also, the fibrils 24A of the first tube 10A are angularly offset from the fibrils 24B of the second tube 10B by an angle γ. The angular offset of the fibrils 24A and 24B provides the prosthesis 100 with resistance against failure not provided by either tube 10A, 10B alone. In a preferred embodiment, with the angles α and β being each at least 10 degrees, the angle γ will be at least 20 degrees. Preferably, the node and fibrils of each of the tubes 10A, 10B are generally-equally angularly offset throughout the respective tube 10A, 10B.

Because the first tube 10A is disposed within the second tube 10B, the second tube 10B is formed dimensionally slightly larger to accommodate the first tube 10A within its lumen 16B.

As an alternative, only one of the tubes 10A, 10B may be twisted. The node and fibrils of the two tubes 10A, 10B would, nevertheless, be angularly offset.

In a preferred manner of preparing the prosthesis 100, the first tube 10A is provided and mounted onto a mandrel where it is twisted into its desired helical configuration. The twisted configuration of the first tube 10A is maintained. The second tube 10B is provided and twisted as desired, and in its twisted state telescoped over the first tube 10A. The first and second tubes 10A and 10B are fixed together using any technique known to those skilled in the art, preferably sintering. Adhesive may also be used to bond the tubes, such as a thermoplastic fluoropolymer adhesive (e.g., FEP). Once fixed, the prosthesis 100 is prepared.

Although reference has been made herein to extruded ePTFE tubes, tubes formed by other techniques may also be used, such as with rolling a sheet, or wrapping a tape. Generally, with these non-extrusion techniques, the fibrils of the ePTFE will not initially be oriented parallel to the longitudinal axis of the tube, but rather transverse thereto. These non-extruded tubes may replace one or more of the tubes 10A, 10B in a non-twisted state or in a twisted state.

Figure 5:
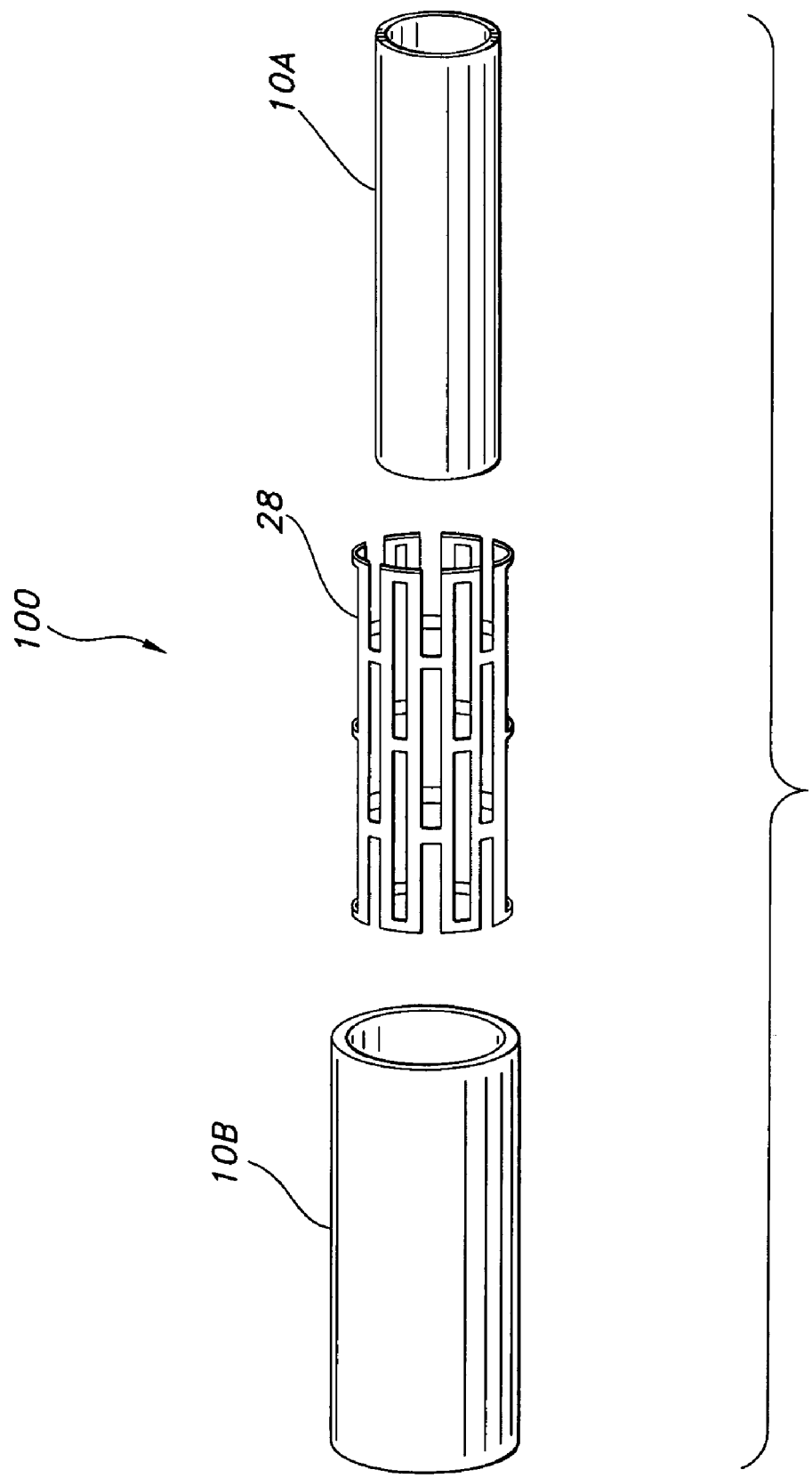

As shown in FIG. 5, the prosthesis 100 may also include a radially expandable support member 28, which may be disposed interiorly of the first tube 10A, exteriorly of the second tube 10B, or interposed between the two tubes 10A, 10B. Additionally, multiple support members located at the aforementioned locations may be provided. The radially expandable support member 28 may be fixed to the tubes 10A, 10B using any technique known to those skilled in the art, such as bonding. Additionally, with the radially expandable support member 28 being interposed between the tubes 10A, 10B, the tubes 10A, 10B may be fixed together through any interstices formed in the radially expandable support member 28.

The radially expandable support member 28 may be of any construction known in the prior art which can maintain patency of the prosthesis 100. For example, as shown in FIG. 5, the radially-expandable support member 28 may be a stent. The particular stent 28 shown in FIG. 5 is fully described in commonly assigned U.S. Pat. No. 5,693,085 to Buirge et al., and the disclosure of U.S. Pat. No. 5,693,085 is incorporated by reference herein. The stent may be an intraluminally implantable stent formed of a metal such as stainless steel or tantalum, a temperature-sensitive material such as Nitinol, or alternatively formed of a superelastic alloy or suitable polymer. Although a particular stent construction is shown with reference to the present invention, various stent types and stent constructions may be employed for the use anticipated herein. Among the various useful radially-expandable support members 28 include, without limitation, self-expanding stents and balloon expandable stents. The stents may be capable of radially contracting as well. Self-expanding stents include those that have a spring-like action which causes the stent to radially expand or stents which expand due to the memory properties of the stent material for a particular configuration at a certain temperature. Other materials are of course contemplated, such as stainless steel, platinum, gold, titanium, tantalum, niobium, and other biocompatible materials, as well as polymeric stents. The configuration of the radially-expandable support member 28 may also be chosen from a host of geometries. For example, wire stents can be fastened in a continuous helical pattern, with or without wave-like forms or zig-zags in the wire, to form a radially deformable stent. Individual rings or circular members can be linked together such as by struts, sutures, or interlacing or locking of the rings to form a tubular stent.

Furthermore, the prosthesis 100 may be used with additional layers which may be formed of polymeric material and/or fabric. Furthermore, any layer or portion of the prosthesis 100, including the tubes 10A, 10B, may be impregnated with one or more therapeutic and pharmacological substances prior to implantation of the prosthesis 100 for controlled release over an extended duration. It is anticipated that the prosthesis 100 can be partially or wholly coated with hydrophilic or drug delivery-type coatings which facilitate long-term healing of diseased vessels. Such a coating is preferably bioabsorbable, and is preferably a therapeutic agent or drug, including, but not limited to, anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

Various changes and modifications can be made in the present invention. It is intended that all such changes and modifications come within the scope of the invention as set forth in the following claims.

What is claimed is:

1. A composite prosthesis comprising:
   a first seamless extruded ePTFE tube having a node and fibril structure;
   a second seamless extruded ePTFE tube positioned concentrically about said first ePTFE tube, the second seamless extruded ePTFE tube having a node and fibril structure; and
   only one of said first and second ePTFE tubes being in a helically twisted state oriented in a first rotational direction, and having been twisted from an initial untwisted state to said helically twisted state,
   wherein the node and fibril structure of said first seamless tube is angularly offset from the node and fibril structure of the second ePTFE tube.

2. A composite prosthesis of claim 1 wherein each of said tubes defines a longitudinal axis and said node and fibril structure of one of said first and second tube is angularly offset from said longitudinal axis.

3. A composite prosthesis of claim 1 wherein each of said first and second tubes are in a helically twisted state oriented in different rotational directions.

4. A composite prosthesis of claim 1 further including a stent positioned between said first and second tubes.

5. A composite prosthesis of claim 1 further including a polymer layer positioned between said first and second tubes.

6. A composite prosthesis of claim 1 wherein at least a portion of said prosthesis is impregnated with at least one of a therapeutic and pharmacological substance.

7. A composite prosthesis of claim 1 wherein said first tube is fixed to said second tube.

8. A composite prosthesis of claim 7 wherein said first and second tubes are fixed by sintering.

9. A composite prosthesis of claim 1 wherein one of said first and second tubes is in a helically twisted state oriented in clockwise direction about a longitudinal axis of the graft and the other of the first and second tubes is in a helically twisted state oriented in counter-clockwise direction about the longitudinal axis of the graft.

10. A prosthesis comprising:
    a first seamless extruded ePTFE tube having a node and fibril structure;
    a second seamless extruded ePTFE tube positioned concentrically about said first ePTFE tube, the second seamless extruded ePTFE tube having a node and fibril structure; and
    one of said first and second seamless extruded ePTFE tubes being in a helically twisted state with a first amount of twisting and having been twisted from an initial untwisted state,
    the other of said first and second seamless extruded ePTFE tubes not having said first amount of twisting,
    wherein the node and fibril structure of said first seamless extruded ePTFE tube is angularly offset from the node and fibril structure of the second seamless extruded ePTFE tube.

11. The prosthesis of claim 10 wherein the other of said first and second seamless extruded ePTFE tubes is in a helically twisted state with a second amount of twisting different from said first amount and having been twisted from an initial untwisted state.

12. The prosthesis of claim 11 wherein one of said first and second seamless extruded ePTFE tubes is twisted in a clockwise direction and the other of said first and second seamless extruded ePTFE tubes is twisted in a counterclockwise direction.

13. The prosthesis of claim 10 wherein the other of said first and second seamless extruded ePTFE tubes is not twisted.

* * * * *